(12) United States Patent
Chow et al.

(10) Patent No.: US 8,183,414 B2
(45) Date of Patent: May 22, 2012

(54) N-(1-PHENYL-2-ARYLETHYL)-4,5-DIHYDRO-2H-PYRROL-5-AMINE COMPOUNDS AS SUBTYPE SELECTIVE MODULATORS OF ALPHA2B OR ALPHA2B AND ALPHA2C ADRENOCEPTORS

(75) Inventors: Ken Chow, Newport Coast, CA (US); Janet A. Takeuchi, Anaheim, CA (US); Ling Li, Irvine, CA (US); Todd M. Heidelbaugh, Fountain Valley, CA (US); Phong X. Nguyen, Placentia, CA (US); Evelyn G. Corpuz, Irvine, CA (US); Wenkui K Fang, Irvine, CA (US); Santosh C. Sinha, Ladera Ranch, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 291 days.

(21) Appl. No.: 12/632,494

(22) Filed: Dec. 7, 2009

(65) Prior Publication Data
US 2010/0145061 A1 Jun. 10, 2010

Related U.S. Application Data

(60) Provisional application No. 61/120,631, filed on Dec. 8, 2008.

(51) Int. Cl.
*C07C 257/00* (2006.01)
*A61K 31/155* (2006.01)

(52) U.S. Cl. ........................................ 564/244; 514/637
(58) Field of Classification Search .................. None
See application file for complete search history.

(56) References Cited

U.S. PATENT DOCUMENTS

| | | | |
|---|---|---|---|
| 3,900,565 A | 8/1975 | Griser et al. | |
| 3,963,701 A | 6/1976 | Griser et al. | |

FOREIGN PATENT DOCUMENTS

| | | |
|---|---|---|
| EP | 0370320 | 5/1990 |
| FR | 2265373 | 10/1975 |
| WO | WO 92/00073 | 1/1992 |
| WO | WO 2008/115141 | 9/2008 |
| WO | WO 2008-123821 | 10/2008 |
| WO | WO 2010029069 A1 * | 3/2010 |

OTHER PUBLICATIONS

CAPLUS 1976:59216.*
Silverman, R. "The Organic Chemistry of Drug Design and Drug Action," 2004, Elsevier, pp. 29-32.*
Messier EPet. al., 1995, Pharmacol. Toxicol. 76, pp. 308-311.
Robert R. Ruffolo, Jr., α-Adrenoreceptors: Molecular Biology, Biochemistry and Pharmacology, (Progress in Basic and Clinical Pharmacology series, Karger, 1991).

* cited by examiner

*Primary Examiner* — Janet Andres
*Assistant Examiner* — Heidi Reese
(74) *Attorney, Agent, or Firm* — Doina G. Ene; John E. Wurst; Kevin J. Forrestal

(57) ABSTRACT

The present invention provides compounds which are N-(1-phenyl-2-arylethyl)-4,5-dihydro-2H-pyrrol-5-amine compounds and are subtype selective modulators of alpha 2B or alpha 2B and alpha 2C adrenoreceptors and are selected from the group of compounds represented by the formula

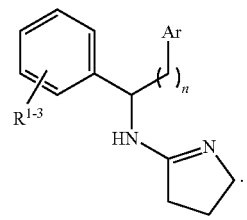

8 Claims, No Drawings

N-(1-PHENYL-2-ARYLETHYL)-4,5-DIHYDRO-2H-PYRROL-5-AMINE COMPOUNDS AS SUBTYPE SELECTIVE MODULATORS OF ALPHA2B OR ALPHA2B AND ALPHA2C ADRENOCEPTORS

CROSS-REFERENCE TO RELATED APPLICATION

This application claims the benefit of U.S. Provisional Patent Application Ser. No. 61/120,631, filed on Dec. 8, 2008, the entire disclosure of which is incorporated herein by this specific reference.

FIELD OF THE INVENTION

This invention relates to pharmaceutical compositions comprising N-(1-phenyl-2-arylethyl)-4,5-dihydro-2H-pyrrol-5-amine compounds. These compounds are subtype selective modulators of α2B or α2B and α2C adrenoceptors and are useful in treating diseases that include but not limited to chronic pain, visceral pain, corneal pain, neuropathic pain, glaucoma, ischemic neuropathies and other neurodegenerative diseases.

DESCRIPTION OF THE RELATED ART

Human adrenergic receptors are integral membrane proteins which have been classified into two broad classes, the α and the β adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: α receptors tend to bind norepinephrine more strongly than epinephrine and much more strongly than the synthetic compound isoproterenol. The preferred binding affinity of these hormones is reversed for the β receptors. In many tissues, the functional responses, such as smooth muscle contraction, induced by α receptor activation are opposed to responses induced by beta receptor binding.

Subsequently, the functional distinction between α and β receptors was further highlighted and refined by the pharmacological characterization of these receptors from various animal and tissue sources. As a result, α and β adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R-(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective α-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the α-adrenergic receptors, one is directed to Robert R. Ruffolo, Jr., α-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting α-adrenergic receptor affinity is explored.

The cloning, sequencing and expression of α receptor subtypes from animal tissues has led to the subclassification of the $\alpha_1$ adrenoreceptors into the $\alpha_{1A}$, $\alpha_{1B}$, and $\alpha_{1D}$ subtypes. Similarly, the $\alpha_2$ adrenoreceptors have also been classified into $\alpha_{2A}$, $\alpha_{2B}$, and $\alpha_{2C}$ receptor subtypes. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having α2 adrenergic receptor agonist activity are known analgesics. However, many compounds having such activity do not provide the activity and specificity desirable when treating disorders modulated by α2 adrenoceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

It is one object of this invention to provide compounds having selectivity at the α2 adrenoreceptors subtypes, e.g. the 2B and/or 2C α adrenergic receptor subtypes.

Other objects of this invention will become apparent from a reading of the present specification.

SUMMARY OF THE INVENTION

The present invention provides compounds which are N-(1-phenyl-2-arylethyl)-4,5-dihydro-2H-pyrrol-5-amine compounds. These compounds are subtype selective modulators of alpha2B or alpha2B and alpha2C adrenoceptors and are useful in treating diseases that include but not limited to chronic pain, visceral pain, corneal pain, neuropathic pain, glaucoma, ischemic neuropathies and other neurodegenerative diseases. More particularly, these compounds are N-substituted 3,4-dihydro-2H-pyrrol-5-amines having selectivity for the alpha 2B or alpha 2B and alpha 2C adrenergic receptors. The compounds of this invention are selected from the group of compounds represented by the formula

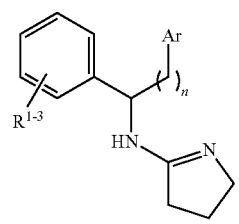

Wherein R is selected from the group consisting of H; lower alkyl; alkenyl; alkynyl; cycloalkyl; aryl; lower alkyloxy; hydroxyl; halogen, e.g. fluoro, chloro, bromo; nitrile; trifluoromethyl; amino; thio, nitro; and carboxy groups;

Ar is an aryl group, e.g. a carbocyclic or heterocyclic aryl group, including, but not limited to, benzene, pyridine, thiophene, furan, naphthalene, quinoline, indan, and benzofuran groups, which aryl group may be bonded to the above moiety at any position and wherein said aryl group may, itself, be substituted with any common organic functional group including but not limited to alkyl, e.g. lower alkyl; alkenyl, e.g. lower alkenyl; alkynyl, e.g. lower alkynyl; aryl; alkoxy, e.g. lower alkyloxy; hydroxyl; halogen, e.g. fluoro, chloro, bromo; nitro; nitrile; trifluoromethyl; amino; thiol and carboxy groups; and n is 0 or an integer of from 1 to 5.

DETAILED DESCRIPTION OF THE INVENTION

Unless otherwise indicated, the following terms as used throughout this specification have the following meanings:
"Me" refers to methyl.
"Et" refers to ethyl.
"tBu" refers to t-butyl.
"iPr" refers to i-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino and SH.

"Alkenyl" refers to a straight-chain, branched or cyclic unsaturated hydrocarbon group containing at least one carbon—carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, $NO_2$, halogen, dimethyl amino and SH.

"Alkynyl" refers to a straight-chain, branched or cyclic unsaturated hydrocarbon containing at least one carbon—carbon triple bond. Preferably, the alkynyl group has 2 to 12 carbons. More preferably it is a lower alkynyl of from 2 to 7 carbons, most preferably 2 to 4 carbons. The alkynyl group may be optionally substituted with one or more substituents selected from the group consisting of hydroxyl, cyano, alkoxy, O, S, $NO_2$, halogen, dimethyl amino and SH.

"Alkoxy" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino "Alkaryl" refers to an alkyl that is covalently joined to an aryl group. Preferably, the alkyl is a lower alkyl.

"Aryloxy" refers to an "O-aryl" group.

"Arylalkyloxy" refers to an "O-alkaryl" group.

"Carbocyclic" refers to cyclic saturated or unsaturated aliphatic hydrocarbon and aryl hydrocarbon groups wherein the ring atoms are exclusively carbons, and comprises from 6 to 20 carbon atoms, including said ring atoms.

"Carbocyclic aryl" refers to an aryl group wherein the ring atoms are carbon.

"Heterocyclic" refers to cyclic groups wherein the ring atoms comprise carbon atoms and at least one oxygen, nitrogen, and/or sulfur atom and may be saturated, unsaturated, i.e. have one or more double bonds, or aryl, and comprises up to 20 carbon atoms and from 1 to 5 of the above heteroatoms.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Ester" refers to —C(O)—O—R', wherein R' is alkyl, aryl or alkylaryl.

"Thioamide" refers to —C(S)—NH—R', wherein R' is alkyl, aryl, alkylaryl or hydrogen.

"Thiol ester" refers to —C(O)—S—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R'''', where R'''' is aryl, C(CN)=C-aryl, $CH_2$ CN, alkyaryl, sulfonamide, NH-alkyl, NH-alkylaryl, or NH-aryl.

Also, alternatively the substituent on the phenyl moiety, as shown below, is referred to as an o, m or p substituent or a 2, 3 or 4 substituent, respectively. (Obviously, the 5 substituent is also a m substituent and the 6 substituent is an o substituent.)

The preferred compounds of this invention are

| Compound | Structure |
|---|---|
| 1 | 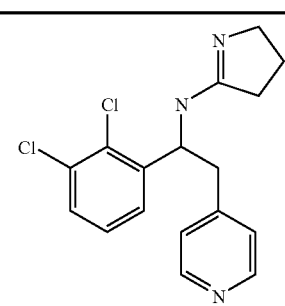 |

-continued
| Compound | Structure |
|---|---|
| 2 | 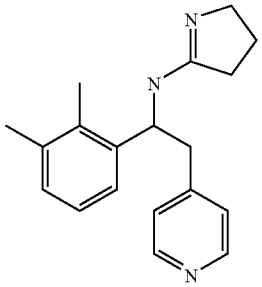 |
| 3 | 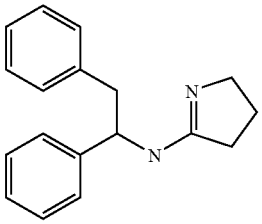 |
| 4 | 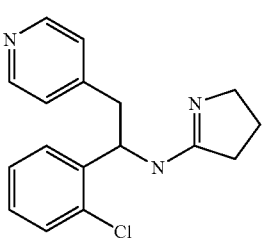 |
| 5 | 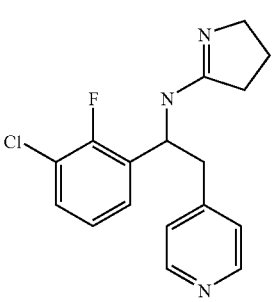 |
| 6 | 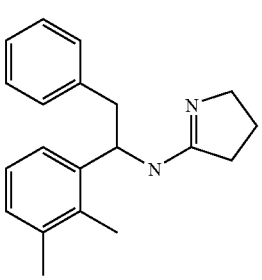 |
-continued
| Compound | Structure |
|---|---|
| 7 | 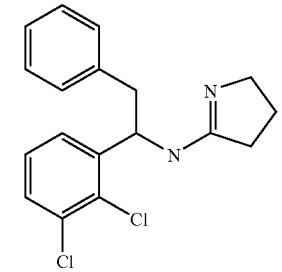 |
| 8 | 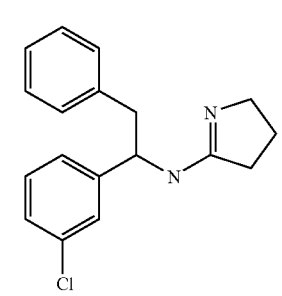 |
| 9 | 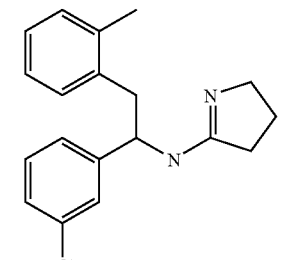 |
| 10 | 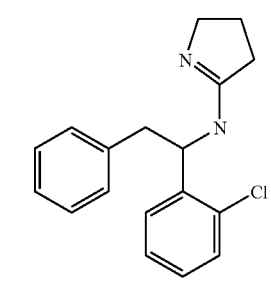 |
| 11 | 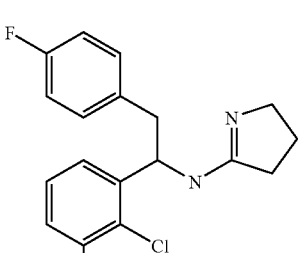 |

| Compound | Structure |
|---|---|
| 12 | 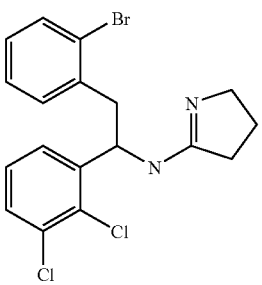 |
| 13 | 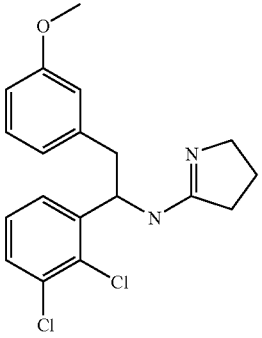 |
| 14 | 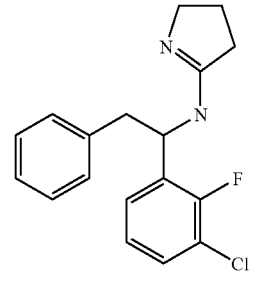 |
| 15 | 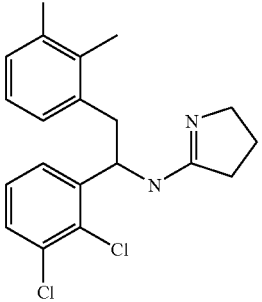 |
| 16 | 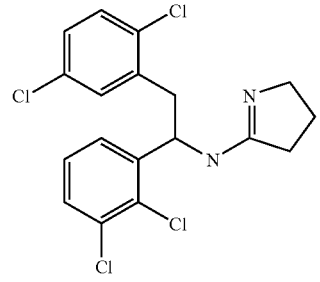 |
| 17 | 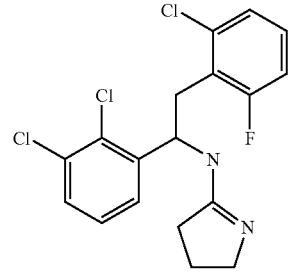 |
| 18 (single enantiomer) | 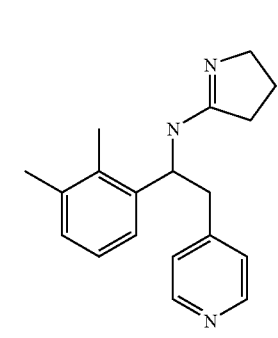 |
| 19 (single enantiomer) | 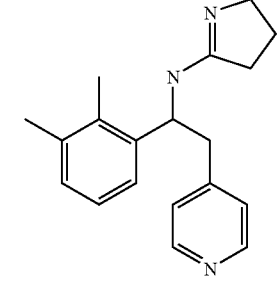 |
| 20 | 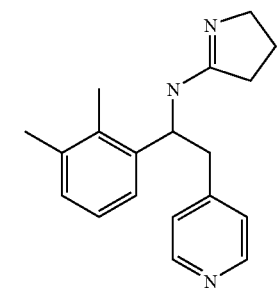 |
| 21 | 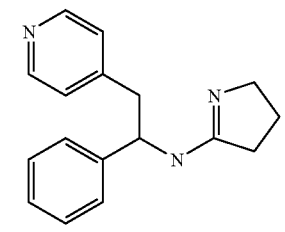 |

| Compound | Structure |
|---|---|
| 22 | 1-(2,3-dichlorophenyl)-2-(2,4-dichlorophenyl)ethyl-N-(pyrrolin-2-yl)amine |
| 23 | 1-(2,3-dichlorophenyl)-3-phenylpropyl-N-(pyrrolin-2-yl)amine |
| 24 | 1-phenyl-2-(pyridin-2-yl)ethyl-N-(pyrrolin-2-yl)amine |
| 25 | 1-phenyl-2-(pyridin-3-yl)ethyl-N-(pyrrolin-2-yl)amine |
| 26 | 1-(2,3-dichlorophenyl)-2-(3,4-dichlorophenyl)ethyl-N-(pyrrolin-2-yl)amine |

| Compound | Structure |
|---|---|
| 27 | 1-(2,3-dimethylphenyl)-2-(pyridin-3-yl)ethyl-N-(pyrrolin-2-yl)amine |
| 28 | 1-(2,3-dichlorophenyl)-2-(pyridin-3-yl)ethyl-N-(pyrrolin-2-yl)amine |
| 29 | 1-(3-chlorophenyl)-2-(5-methylpyridin-3-yl)ethyl-N-(pyrrolin-2-yl)amine |
| 30 | 1-(3-chlorophenyl)-2-(2-chloropyridin-3-yl)ethyl-N-(pyrrolin-2-yl)amine |
| 31 | 1-(3-chlorophenyl)-2-(6-chloropyridin-3-yl)ethyl-N-(pyrrolin-2-yl)amine |

| Compound | Structure |
|---|---|
| 32 | 3-bromo-4-methylpyridine with CH at 3-chlorophenyl linked to 4,5-dihydro-pyrrol-2-ylamine |
| 33 | 4,5-dimethylpyridine with CH at 3-chlorophenyl linked to 4,5-dihydro-pyrrol-2-ylamine |
| 34 | 4,5-dimethylpyridine with CH at 3-methylphenyl linked to 4,5-dihydro-pyrrol-2-ylamine |

Novel compounds having this general structure were synthesized and tested for alpha adrenergic activity using the Receptor Selection and Amplification Technology (RSAT) assay (Messier et. al., 1995, Pharmacol. Toxicol. 76, pp. 308-311). Cells expressing each of the alpha-2 adrenergic receptors alone were incubated with the various compounds and a receptor-mediated growth response was measured. The compounds activity is described as its EC50 and relative efficacy compared to a standard full agonist. The results are reported in Table 1, below.

TABLE 1

Biological Data: EC50 and Intrinsic Activity (NA = not active)

| | RSAT EC50 (nM)/(Rel Eff) | | |
|---|---|---|---|
| Compound | α2A | α2B | α2C |
| 1 | NA | 8.9 (1.25) | 48.4 (0.59) |
| 2 | NA | 8.7 (1.04) | 84.8 (0.37) |
| 3 | NA | 21.3 (0.63) | 14.1 (0.36) |
| 4 | NA | 38.4 (0.57) | 10.3 (0.56) |
| 5 | NA | 10.8 (0.94) | NA |
| 6 | NA | 2.9 (0.72) | NA |
| 7 | NA | 6.6 (0.88) | NA |
| 8 | NA | 11.6 (0.71) | NA |
| 9 | NA | 3.2 (0.62) | 2.8 (0 30) |
| 10 | NA | 12.0 (0.51) | 13.3 (0.37) |
| 11 | NA | 8.0 (0.80) | NA |
| 12 | NA | 8.7 (0.96) | NA |
| 13 | NA | 4.0 (0.97) | 12.9 (0.36) |
| 14 | NA | 8.6 (0.96) | 6.3 (0.36) |
| 15 | NA | 12.8 (0.70) | NA |
| 16 | NA | 10.5 (1.04) | 12.5 (0.35) |
| 17 | NA | 19.5 (0.73) | NA |
| 18 | NA | 3.1 (0.93) | 19.6 (0.43) |
| 19 | NA | 210.4 (0.58) | NA |
| 20 | NA | 2.2 (1.18) | 17.1 (0.46) |
| 21 | NA | 59.2 (0.81) | 39.6 (0.34) |
| 22 | NA | 7.1 (1.03) | NA |
| 23 | NA | 57.0 (0.69) | NA |
| 24 | NA | 214.3 (0.44) | NA |
| 25 | NA | 81.7 (0.74) | NA |
| 26 | NA | 8.6 (0.93) | NA |
| 27 | NA | Potent (1.04) | NA |
| 28 | NA | Potent (1.19) | NA |
| 29 | 293 (0.31) | Potent (1.1) | 29.8 (0.36) |
| 30 | NA | Potent (1.09) | NA |
| 31 | NA | 67.2 (0.84) | NA |
| 32 | NA | 11.2 (0.92) | NA |
| 33 | NA | 19.9 (0.91) | NA |
| 34 | NA | 5.1 (0.85) | NA |

As may be determined from Table 1, the preferred compounds of this invention are as follows:

R is preferably selected from the group consisting of H, halogen, e.g. fluoro or chloro, and lower alkyl, e.g. methyl.

Ar is preferably selected from the group consisting of phenyl, which may be unsubstituted or substituted, e.g. disubstituted, with one or two halogen groups e.g. fluoro, chloro, or bromo and/or one lower alkyl, e.g. methyl, and/or one lower alkoxy, e.g. methoxy and pyridyl, which may be unsubstituted or substituted, e.g. disubstituted, with one or two lower alkyl groups, e.g. methyl, and/or halogen groups, e.g. chloro or bromo.

For compounds of the present invention, wherein there is selectivity for the 2B adrenergic receptor subtype and the absence of any 2C adrenergic receptor subtype activity, R is preferably H or mono or dichloro or mono or dimethyl or fluoro, chloro and the aryl, i.e. Ar, is selected from the group consisting of phenyl, which may be unsubstituted or substituted, e.g. disubstituted, with one or two halogen groups, e.g. fluoro, chloro, or bromo and/or one lower alkyl, e.g. methyl, and/or one lower alkoxy, e.g. methoxy, and pyridyl, which may be unsubstituted or substituted, e.g. disubstituted, with one or two lower alkyl groups, e.g. methyl, and one halogen group, e.g. bromo/ or one halogen group, e.g. chloro.

In the most active compounds of this invention, i.e. where the EC50 activity is less than 5 nM and/or is designated as potent, R is preferably dimethyl or mono or dichloro and Ar is selected from the group consisting of phenyl, which may be unsubstituted or substituted with two chloro groups or one methyl group or one methoxy group, and pyridyl which may be unsubstituted or substituted with methyl or chloro.

The compounds in this invention will be useful for the treatment of mammals, including humans, with a wide range of therapeutic areas, including but not limited to hypertension, congestive heart failure, asthma, depressions, glaucoma, elevated intraocular pressure, ischemic neuropathies, optic neuropathy, pain, visceral pain, corneal pain, headache pain, migraine, cancer pain, back pain, irritable bowl syndrome pain, muscle pain, pain associated with diabetic neuropathy, the treatment of diabetic retinopathy, other retinal degenerative conditions, stroke, cognitive deficits, neuropsychiatric conditions, drug dependence, withdrawal symptoms, obsessive compulsive disorder, obesity, insulin resistance, stress related conditions, diarrhea, diuresis, nasal congestions, spasticity, attention deficit disorder, psychoses, anxiety, autoimmune disease, Crohn's disease, gastritis, Alzheimer's, Parkinson's, ALS, and other neurodegenerative diseases.

The compounds of this invention may be prepared as follows:

Syntheses of the Amines:

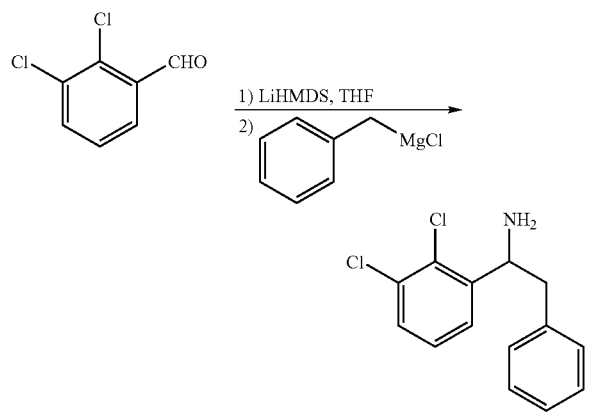

General Procedure 1

1-(2,3-dichlorophenyl)-2-phenylethanamine-

To 2,3-dichlorobenzaldehyde (2.58 g, 19.2 mmol) in THF (5 mL) at 0° C. was added lithium bis(trimethylsilyl)amide (1M in THF, 23 mL). The ice-water bath was removed and the reaction mixture was stirred from 0° C. to room temperature for 2 h. The reaction mixture was then cooled back to 0° C. and benzylmagnesium chloride (1M in THF, 23 mL) was added. The reaction mixture was stirred from 0° C. to room temperature for 1 h then quenched with $NH_4Cl$ (Sat.), extracted with ethyl acetate. Combined ethyl acetate was washed with brine, dried over sodium sulfate and concentrated. HCl (1.25M in methanol) was added to the above residue until a pH of 2 to form the amine salt solution. Methanol was removed to give yellow solid. To the solid was added dichloromethane. The suspension was filtered and washed with dichloromethane to yield white solid as pure amine salt. The amine salt was converted to free amine by dissolving the white solid in methanol, basified with NaOH (1N) and extracted with ethyl acetate. Combined ethyl acetate was washed with brine, dried over sodium sulfate and concentrated to produce 1-(3-chloro-2-methylphenyl)-2-phenylethanamine (3.26 g, 75%) as light yellow oil. $^1$H NMR (300 MHz, $CDCl_3$) δ 2.57-2.65 (m, 1H), 3.11-3.17 (m, 1H), 4.68-4.72 (m, 1H), 7.20-7.35 (m, 6H), 7.36-7.40 (m, 1H), 7.51-7.54 (m, 1H).

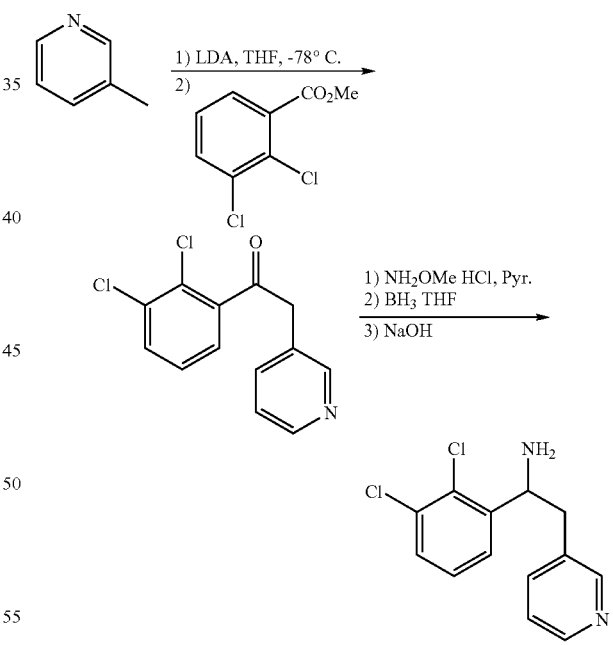

General Procedure 2

1-(2,3-dichlorophenyl)-2-(pyridin-3-yl)ethanone-

To lithium diisopropyl amide (20 mL, 1.5 M in cyclohexane, 30 mmol) in THF (50.0 mL) at −78° C. was added a solution of 3-picoline (2.79 g, 30 mmol) in THF (25.0 mL) drop wise and stirred at −78° C. for 0.5 hours. The dry ice bath was removed and the reaction mixture was stirred at room temperature 1 hour. The mixture was then cooled to 0° C. and a solution of methyl 2,3-dichlorobenzoate (6.15 g, 30 mmol) in THF (25.0 mL) was added drop wise. The reaction mixture was warmed to room temperature and stirred overnight. The reaction was quenched with ammonium chloride and extracted with ethyl acetate (2×). Combined ethyl acetate phase was washed with brine, dried over magnesium sulfate and concentrated. Purification by chromatography on silica gel (70% ethyl acetate/hexane) gave 1-(2,3-dichlorophenyl)-2-(pyridin-3-yl)ethanone (1.07 g, 13%) as brown oil.

$^1$H NMR (300 MHz, CDCl$_3$) δ 4.24 (s, 2H), 7.24-7.32 (m, 3H), 7.55-7.59 (m, 1H), 7.62-7.66 (m, 1H), 8.48-8.49 (m, 1H), 8.53-8.55 (m, 2H).

1-(2,3-dichlorophenyl)-2-(pyridin-3-yl)ethanamine-

To a solution of 1-(2,3-dichlorophenyl)-2-(pyridin-3-yl)ethanone (1.07 g, 4.03 mmol) in pyridine (10 mL) was added methoxylamine hydrochloride (674 mg, 8.07 mmol) in one portion at room temperature. The resulting mixture was stirred at 50° C. for one hour. The pyridine was removed in vacuo, and residue was added water and extracted with ethyl acetate. Ethyl acetate phase was washed with brine, dried over magnesium sulfate and concentrated. Purification by chromatography on silica gel (50% ethyl acetate/hexane) gave a mixture of geometrical oxime isomers (820 mg, 69%) as brown oil.

To a solution of a mixture of syn- and anti-oxime, (820 mg, 2.78 mmol) in THF (10 mL) at room temperature was added borane-THF complex (1M, 11.1 mL). The resulting solution was refluxed for 3 hours, and cooled to 0° C. Water was carefully added followed by 20% NaOH. The resulting mixture was refluxed overnight. The mixture was cooled to room temperature and extracted with ethyl acetate (2×). Combined ethyl acetate phase was washed with brine, dried over magnesium sulfate and concentrated. Purification by chromatography on silica gel (ethyl acetate) gave 1-(2,3-dichlorophenyl)-2-(pyridin-3-yl)ethanamine (632 mg, 85%) as yellow solid.

$^1$H NMR (300 MHz, CD$_3$COCD$_3$) δ 2.75-2.83 (m, 1H), 2.99-3.06 (m, 1H), 4.64-4.68 (m, 1H), 7.22-7.27 (m, 1H), 7.32-7.37 (m, 1H), 7.44-7.48 (m, 1H), 7.57-7.61 (m, 1H), 7.65-7.68 (m, 1H), 8.40-8.42 (m, 2H).

Synthesis of
N-(1,2-diarylethyl)-4,5-dihydro-2H-pyrrol-5-amine compounds

Scheme 3

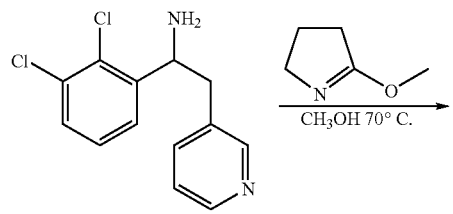

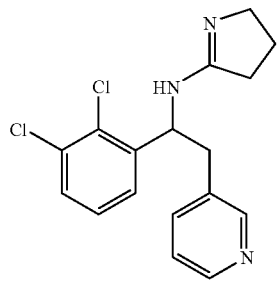

General Procedure 3

N-(1-(2,3-dichlorophenyl)-2-(pyridin-3-yl)ethyl)-3,4-dihydro-2H-pyrrol-5-amine (28)-

To 1-(2,3-dichlorophenyl)-2-(pyridin-3-yl)ethanamine (258 mg, 0.97 mmol) in methanol (5 mL) was added 5-methoxy-3,4-dihydro-2H-pyrrole (96 mg, 0.97 mmol) followed by acetic acid (2 drops). The mixture was heated at 70° C. for 16 hours. The mixture was cooled to room temperature and methanol was removed. Purification by chromatography on silica gel (5% 7N NH$_3$ in MeOH/CH$_2$Cl$_2$) gave N-(1-(2,3-dichlorophenyl)-2-(pyridin-3-yl)ethyl)-3,4-dihydro-2H-pyrrol-5-amine (161 mg, 50%) as an off white solid.

$^1$H NMR (300 MHz, CD$_3$OD) δ 1.79-1.90 (m, 2H), 2.41-2.49 (m, 2H), 2.87-2.94 (m, 1H), 3.14-3.21 (m, 1H), 3.34-3.41 (m, 2H), 5.28-5.33 (m, 1H), 7.30-7.47 (m, 4H), 7.77-7.81 (m, 1H), 8.36-8.42 (m, 1H), 8.43 (s, 1H).

Compounds 3, 6, 7, 8, 9, 10, 11, 12, 13, 14, 15, 16, 17, 20, 22, 23 and 26 were synthesized according to General Procedure 1 and 3

Compounds 1, 2, 4, 5, 18, 19, 21, 24, 25, 27, 28, 29, 30, 31, 32, 33 and 34 were synthesized according to General Procedure 2 and 3. There are modifications in General Procedure 2 for some compounds in terms of reaction time and temperature. While not intending to limit the scope of this invention in any way, of particular interest are the following compounds.

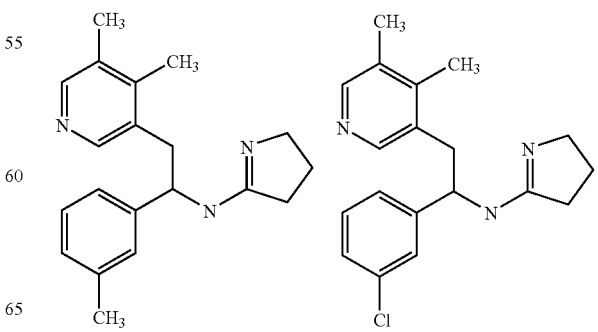

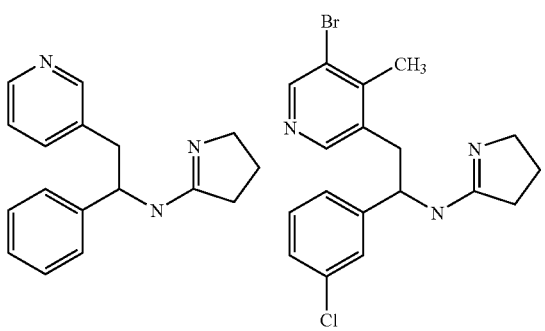

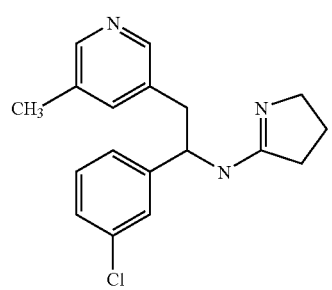

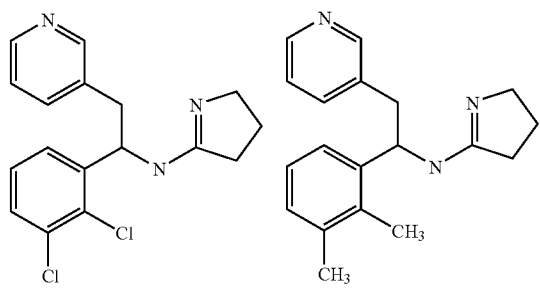

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

What is claimed is:

1. N—(1-phenyl-2-arylethyl)-4,5-dihydro-2H-pyrrol-5-amine compounds represented by the formula

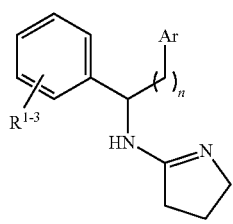

wherein R is selected from the group consisting of H, lower alkyl, alkenyl, alkynyl, cycloalkyl, aryl, lower alkyloxy, hydroxyl, halogen, nitrile, trifluoromethyl, amino, thio, nitro and carboxy groups; Ar is a 3-pyridyl group which may be unsubstituted or may be substituted, and n is 1.

2. A compound according to claim 1 wherein Ar is unsubstituted or is substituted with one or more alkyl, or halogen groups.

3. A compound according to claim 1 wherein R is selected from the group consisting of H, lower alkyl, fluoro, chloro and bromo groups.

4. A compound according to claim 3 wherein R is selected from the group consisting of H, fluoro, chloro, and methyl.

5. A compound according to claim 2 wherein Ar is 3-pyridyl which may be unsubstituted or substituted with one or two methyl groups, and one bromo group or one chloro group.

6. A compound according to claim 5 wherein R is H, fluoro, chloro or methyl and there are 1 to 3 R groups, and Ar is 3-pyridyl, which may be unsubstituted or substituted with one methyl group and one bromo, or with one methyl group, or with one chloro group, or with two methyl groups.

7. A compound according to claim 6 having activity at the 2B adrenergic receptor subtype, wherein the EC50 activity is less than 5 nM, wherein R is methyl or chloro and there are 1 to 3 R groups and Ar is 3-pyridyl which may be unsubstituted or substituted with one methyl or one chloro group.

8. A compound according to claim 1 selected from the group consisting of

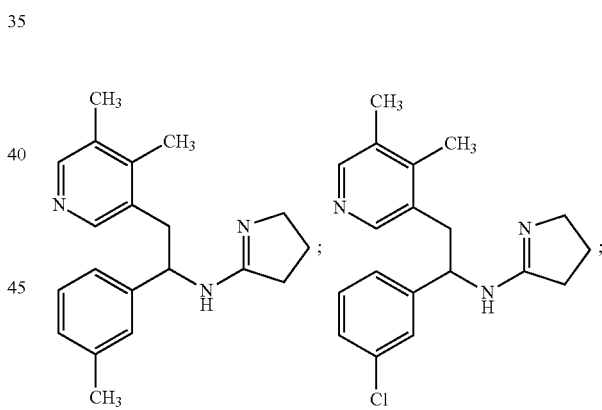

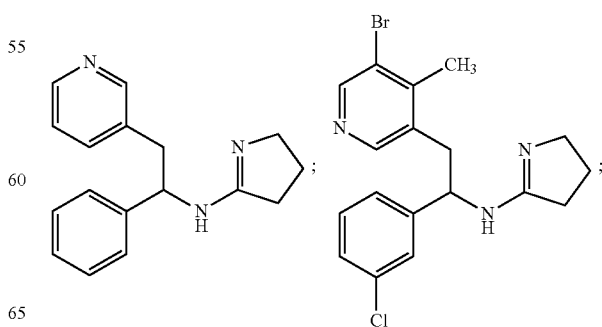

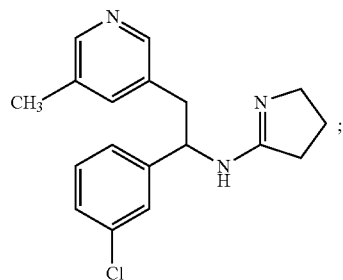
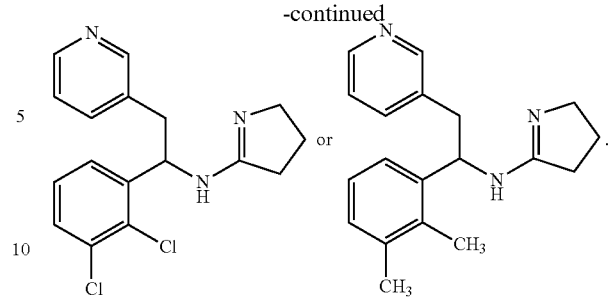
* * * * *